(12) United States Patent
Sylvester et al.

(10) Patent No.: US 7,592,174 B2
(45) Date of Patent: Sep. 22, 2009

(54) ISOLATION OF MESENCHYMAL STEM CELLS

(75) Inventors: Karl G. Sylvester, Los Altos, CA (US); Monika Tataria, St. Louis, MO (US); Laurie Ailles, Palo Alto, CA (US); Irving L. Weissman, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 45 days.

(21) Appl. No.: 11/704,611

(22) Filed: Feb. 9, 2007

(65) Prior Publication Data

US 2007/0292872 A1    Dec. 20, 2007

Related U.S. Application Data

(63) Continuation-in-part of application No. 10/449,795, filed on May 30, 2003, now Pat. No. 7,217,568.

(60) Provisional application No. 60/771,973, filed on Feb. 10, 2006, provisional application No. 60/384,529, filed on May 31, 2002, provisional application No. 60/431,655, filed on Dec. 6, 2002.

(51) Int. Cl.
*C12N 5/00* (2006.01)
*C12N 15/00* (2006.01)
(52) U.S. Cl. .................. 435/325; 435/455; 435/320.1
(58) Field of Classification Search .............. 435/320.1, 435/325, 455
See application file for complete search history.

(56) References Cited

OTHER PUBLICATIONS

Zhou L, Flourescence-based functional assay for Wnt/beta-catenin signaling activity, 2002, Biotechniques, vol. 33, pp. 1126-1135.*
Song X, wingless signaling regulates the maintenance of ovarian somatic stem cells in Drosophila, 2003, Development, vol. 130, pp. 3259-3268.*
Baksh et al., "Adult mesenchymal stem cells: characterization, differentiation, and application in cell and gene therapy", J Cell Mol Med, 2004, 8(3):301-16.
Fujimura et al., "Neural differentiation of adipose-derived stem cells isolated from GFP transgenic mice", Biochem Biophys Res Commun, 2005, 333(1):116-21.
Gronthos et al., "Surface protein characterization of human adipose tissue-derived stromal cells", J Cell Physiol, 2001, 189(1):54-63.
Jiang et al., "Pluripotency of mesenchymal stem cells derived from adult marrow", Nature, 2002, 418(6893):41-9.
Kuznestov, "Single-colony derived strains of human marrow stromal fibroblasts form bone after transplantation in vivo", J Bone Miner Res, 1997, 12(9):1335-47.
Peister et al., "Adult stem cells from bone marrow (MSCs) isolated from different strains of inbred mice vary in surface epitopes, rates of proliferation, and differentiation potential", Blood, 2004, 103(5):1662-8.
Pittenger et al., "Multilineage potential of adult human mesenchymal stem cells", Science, 284:143-7, (1999).
Simmons et al., "Isolation, characterization and functional activity of human marrow stromal progenitors in hemopoiesis", Prog Clin Biol Res, 1994, 389:271-80.
Zuk et al., "Human adipose tissue is a source of multipotent stem cells", Mol. Biol. Cell, 2002, 13(12):4279-95.

* cited by examiner

*Primary Examiner*—Peter Paras, Jr.
*Assistant Examiner*—David Montanari
(74) *Attorney, Agent, or Firm*—Bozicevic, Field & Francis LLP; Pamela J. Sherwood

(57) ABSTRACT

Methods and compositions are provided for the identification and isolation of mammalian mesenchymal stem cells. The methods of the invention provide a means to obtain substantially homogeneous MSC populations. In some embodiments, the homogeneous MSC composition is stable in non-differentiating culture conditions, where the proportion of cells in the composition that have an MSC phenotype are maintained over multiple passages.

8 Claims, 11 Drawing Sheets
(7 of 11 Drawing Sheet(s) Filed in Color)

FIGURE 2
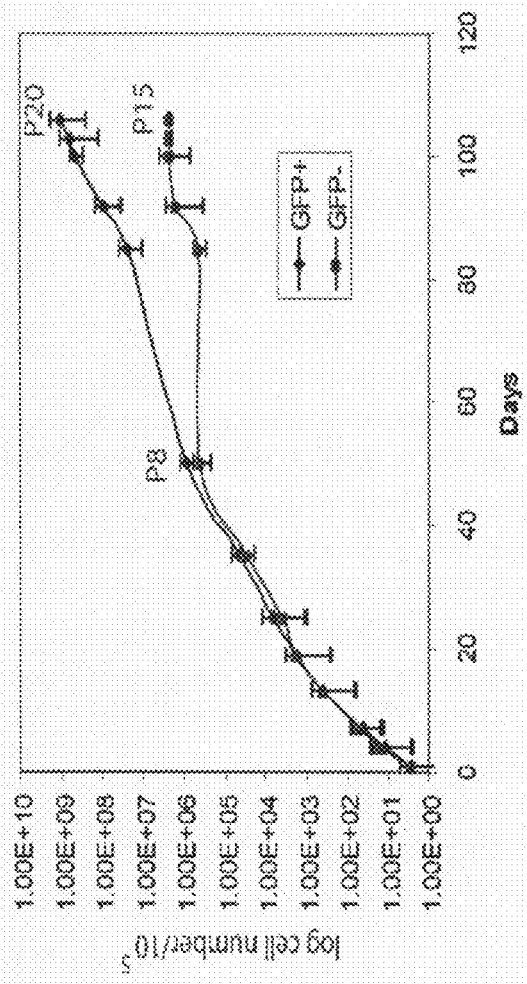
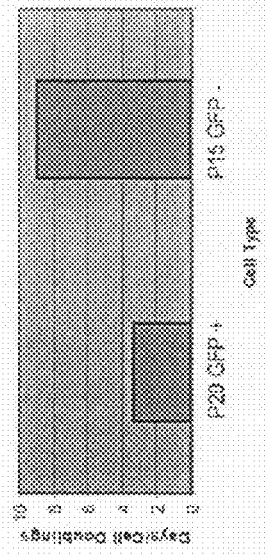
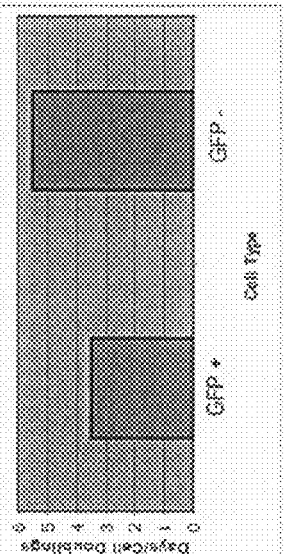

SEQUENCE LISTING

<160> NUMBER OF SEQ ID NOS: 3

<210> SEQ ID NO 1
<211> LENGTH: 11
<212> TYPE: DNA
<213> ORGANISM: human

<400> SEQUENCE: 1
gctttgatct t                                                          11

<210> SEQ ID NO 2
<211> LENGTH: 10
<212> TYPE: DNA
<213> ORGANISM: human

```
<400> SEQUENCE: 2
gatcaaaggg                                                              10

<210> SEQ ID NO 3
<211> LENGTH: 9
<212> TYPE: DNA
<213> ORGANISM: Artificial Sequence
<220> FEATURE:
<223> OTHER INFORMATION: synthetic binding motif

<400> SEQUENCE: 3 sctttgrty                                                                9
```

ISOLATION OF MESENCHYMAL STEM CELLS

This invention was made with Government support under contract EZ1 DE015368-02 awarded by the National Institutes of Health. The Government has certain rights in this invention.

The bone marrow stroma was originally thought to function mainly as a structural framework for the hematopoietic component of the marrow. Since then, it has become well established that the stroma consists of a heterogeneous population of cells, a subset of which exerts both positive and negative regulatory effects on the proliferation and differentiation of hematopoietic stem cells (HSC) in the marrow through a combination of physical and chemical signals. The stroma also contains other non-hematopoietic cells termed mesenchymal stem cells (MSC), which are capable of both self renewal and differentiation into osteoblasts, adipocytes, myoblasts and chondroblasts. MSC are similar to HSC in that they are very rare, existing at an estimated frequency of about 1 in 100,000 bone marrow cells. MSC also give rise to a variety of mature cell types via a step-wise maturation process similar to hematopoiesis, termed mesengenesis.

The observation that MSC are the physiologic precursor cells for a variety of mesenchymal tissues such as bone and adipose has been confirmed in numerous animal models and in humans. More recently, MSC have been harvested from the supportive stroma of a variety of tissues. In both mouse and human a candidate population of cells has been identified in subcutaneous adipose tissue (AMSC). These cells have demonstrated the same in vitro differentiation capacity as BM-MSC for the mesenchymal lineages, osteoblasts, chondrocytes, myocytes, neurons, and adipocytes (Zuk et al. (2002) Mol Biol Cell 13, 4279-95; Fujimura et al. (2005) Biochem Biophys Res Commun 333, 116-21). Additionally, cell surface antigen profiling of these cells has revealed similar cell surface marker characteristics as the more widely studied BM-MSC (Simmons et al. (1994) Prog Clin Biol Res 389, 271-80; and Gronthos et al. (2001) J Cell Physiol 189, 54-63).

Despite the definitions ascribed to MSC populations by their in vitro differentiation capabilities, the mechanisms governing their proliferation and multi-lineage differentiation capacity have been poorly understood. At the clonal level, there is little evidence for MSC self-renewal, therefore these cells might be termed multipotent progenitor cells. One of the greatest obstacles in the study of MSC biology is the heterogeneity of studied cell populations (Baksh et al. (2004) J Cell Mol Med 8, 301-16). For example, Pittenger et al. (1999) Science 284, 143-7 found that the majority of human bone marrow derived MSC are not pluripotent, while Kusnestov et al., (1997) J Bone Miner Res 12, 1335-47 showed that only 58.8% of human MSCs had in vivo osteogenic potential. Others have shown that within the adipose derived populations of MSC, cells with multi-lineage differentiation capability co-exist with single lineage committed cells (Zuk et al. (2002) Mol Biol Cell 13, 4279-95). Other have reported pluripotent progenitor cells (Jiang et al. (2002) Nature 418, 41-9).

This heterogeneity may be explained by the hypothesis that true "mesenchymal stem cells" (cells with the ability to self-renew and differentiate into multiple lineages) are only a small sub-population of the pool of cells termed MSCs, and the remainder of the mixed population consists of cells at various stages of differentiation and commitment. Adding to the complexity of heterogeneity within a single MSC population is the variety of tissues from which MSC have been harvested, and the variety of techniques that have been utilized in their isolation and propagation (Gronthos et al. (2001) J Cell Physiol 189, 54-63; Peister et al. (2004) Blood 103, 1662-8). Given these inconsistencies, it is unlikely that equivalent populations of cells have thus far been compared.

There are no universally accepted antigenic determinants of MSC. The SH2 and SH3 antibodies (see U.S. Pat. No. 5,486,359), which are reported to be markers of MSC, have been shown to recognize CD105 and CD73, respectively. It has also been reported that CD29, CD44, and CD90 are important determinants, and that MSC may be negative for CD45 and CD34. However, Prockop (1997) Science 276, 71-4 reports that their RS cells cannot be clearly distinguished from other adherent mesenchymal cells solely by antigen expression. Other determinants have also been studied, for a more extensive review see, Cytotherapy 2:387-388, 2000.

Preclinical and early clinical safety studies are paving the way for further applications of these cells in the field of transplantation with respect to hematopoietic support, immunoregulation, graft facilitation, and potentially gene therapy. Preclinical studies suggest mesenchymal stem cells can enhance the ability of the bone marrow microenvironment to support hematopoiesis after stem cell transplantation. Moreover, an important role in immunoregulation is suggested by reports that these cells can suppress T cell activation without inducing allogeneic anergy. These findings may have important applications for stem cell transplantation, organ transplantation, and other regenerative and reparative therapies.

Among reported clinical trials, unmanipulated bone marrow has been infused into children with a genetic disorder of brittle bones termed osteogenesis imperfecta (OI). In this study there was an improvement in axial growth and fracture rate of children with OI receiving BMT in whom mesenchymal cells were demonstrated to engraft outside the bone marrow. Autologous mesenchymal cells have been infused in patients undergoing PBSC autografting for breast cancer in an effort to enhance hematopoietic recovery. Autologous gene marked mesenchymal cells have also been infused into adults undergoing autografting for cancer; gene marked cells were found in the marrow 6-8 months after infusion.

The therapeutic implication of these studies for hematopoietic and non-hematopoietic stem cell transplantation is tremendous. However, the ability to identify the most appropriate population and assay methods that characterize the clinical potential of candidate human mesenchymal stem cells are currently lacking. Isolation and characterization standards would permit the comparison of results and this would significantly enhance multi-disciplinary, collaborative approaches to these important problems. Studies in this area will help ensure that future clinical protocols will be based on a solid foundation of basic science.

SUMMARY OF THE INVENTION

Methods and compositions are provided for the identification and isolation of mammalian mesenchymal stem cells. The methods of the invention provide a means to obtain substantially homogeneous MSC populations. MSC may be characterized, for example, with the phenotype of being capable of differentiating into multiple lineages; as being responsive to canonical wnt signaling; as being capable of self-renewal; and the like. In some embodiments, the homogeneous MSC composition is stable in non-differentiating culture conditions, where the proportion of cells in the composition that have an MSC phenotype are maintained over multiple passages.

In one embodiment of the invention, a nucleic acid construct is introduced into a population of cells comprising candidate MSC, which may be a mixed population of primary cells, e.g. bone marrow; adipose tissue, etc.; a mixed population of cultured cells, e.g. bone marrow cultured cells; and the like. The construct comprises sequences encoding a detectable marker, which marker is operably linked to a transcriptional response element regulated by β-catenin. In the presence of active, nuclear β-catenin, the detectable marker is expressed, and indicates that a cell is an MSC responsive to canonical wnt signaling. In some embodiments of the invention, the detectable marker is a fluorescent protein, e.g. green fluorescent protein (GFP) and variants thereof. Viable cells expressing the detectable marker can be sorted to isolate or enrich for MSC.

In another embodiment, mesenchymal stem cells responsive to canonical wnt signaling are enriched by a sorting method, as described above. The cells are then cultured under non-differentiating conditions for at least one passage and not more than about 5 passages. The passaged cells are then sorted again to enrich for mesenchymal stem cells responsive to canonical wnt signaling. Following such a procedure it is found that the resulting population of MSC have a stable phenotype in culture.

Substantially homogeneous MSC, e.g. those that have been enriched for a phenotype of interest, can be maintained in culture, e.g. for expansion; differentiation into cells of interest, e.g. osteoblasts, adipocytes, myoblasts, chondroblasts; etc. The cells can also find use in therapeutic methods, e.g. as a source of osteochondroprogenitors; for treatment of osteogenesis imperfecta; as immunomodulatory agents, e.g. for co-transplantation with a source of hematopoietic stem cells, with solid tissue transplantation; and the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2. Long-term growth assay of cells sorted by responsiveness to β-catenin. The GFP+ and − cells had similar rates of growth. After eight passages the GFP+ cells began to grow at a faster rate than the GFP− cells. Cell doubling time of passage eight GFP+ cells was 3.59±0.05 days and the doubling time of GFP− cells was 6.04±0.03 days (A). After 102 days in culture the GFP+ cells were at passage twenty and had a doubling time of 3.53±0.3 days the GFP− cells were at passage fifteen with a doubling time of 9.20±0.8 days (B).

DETAILED DESCRIPTION OF THE EMBODIMENTS

Figure 1:
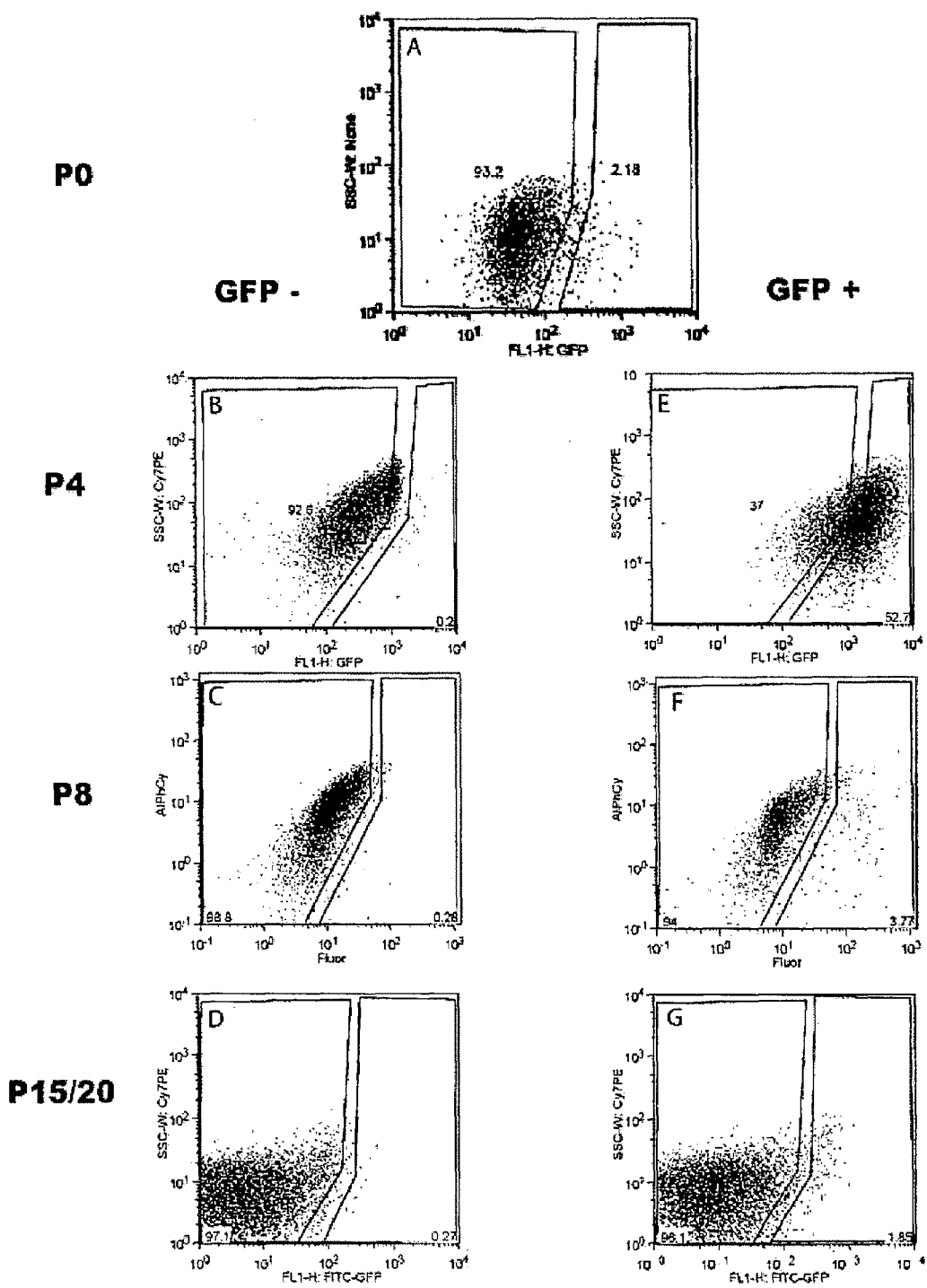
FIG. 1A-1G. FACS plots of MSCs transduced with TCF/LEF-GFP lentivirus. Representative plots were chosen. At passage zero 2.75±1.3% of cells were GFP positive (A). The GFP+ and GFP− cells were sorted and cultured separately. At passage four 51.8±11.6% of the β-catenin responsive (GFP+) cells remained GFP+ (B). At passage eight 2.1±1.23% of the β-catenin responsive cells remained GFP+ (C). At passage twenty 1.19±0.4% the β-catenin responsive cells remained GFP+ (D). The GFP− or β-catenin unresponsive cells remained GFP− at passages four, eight, and fifteen (E-G).

Substantially homogeneous cellular compositions of mesenchymal stem cells (MSC) are provided. MSC may be characterized, for example, with the phenotype of being capable of differentiating into multiple lineages; as being responsive to canonical wnt signaling; as being capable of self-renewal; and the like. In some embodiments, the homogeneous MSC composition is stable in non-differentiating culture conditions, where the proportion of cells in the composition that have an MSC phenotype are maintained over multiple passages. In one embodiment of the invention, a nucleic acid construct comprising sequences encoding a detectable marker, which marker is operably linked to a transcriptional response element regulated by β-catenin, is introduced into a population of cells comprising MSC. In the presence of active, nuclear β-catenin, the detectable marker is expressed. Viable cells expressing the detectable marker can be sorted to isolate or enrich for MSC; and are optionally recultured and resorted.

Mesenchymal Stem Cell (MSC). As used herein, the term MSC refers to a cell capable of giving rise to differentiated cells in multiple mesenchymal lineages, specifically to osteoblasts, adipocytes, myoblasts and chondroblasts. Generally, mesenchymal stem cells also have one or more of the following properties: an ability to undergo asynchronous, or symmetric replication, that is where the two daughter cells after division can have different phenotypes; extensive self-renewal capacity; and clonal regeneration of the tissue in which they exist, for example, the non-hematopoietic cells of bone marrow. "Progenitor cells" differ from stem cells in that they typically do not have the extensive self-renewal capacity. In contrast to previously reported MSC and multipotent mesenchymal cell populations, the cells of the invention do not require lengthy time in culture prior to the appearance of the MSC phenotype, i.e. cells with the MSC phenotype and are responsive to canonical wnt signaling pathways are present in freshly isolated or primary cultures that have been cultured for less than about 20 passages; usually less than about 10 passages.

MSC may be characterized by both the presence of markers associated with specific epitopes identified by antibodies and the absence of certain markers as identified by the lack of binding of specific antibodies. MSC may also be identified by functional assays both in vitro and in vivo, particularly assays relating to the ability of stem cells to give rise to multiple differentiated progeny; assays for responsiveness to canonical wnt signaling; and the like.

The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

The cells which are employed may be fresh, frozen, or have been subject to prior culture. They may be fetal, neonate, adult. MSC may be obtained from adipose tissue (see U.S. patent application Ser. No. 20030082152); bone marrow (Pittenger et al. (1999) Science 284(5411):143-147; Liechty et al. (2000) Nature Medicine 6:1282-1286); G-CSF or GM-CSF mobilized peripheral blood (Tondreau et al. (2005) Stem Cells 23(8): 1105-1112), or any other conventional source.

The methods of the invention provide for substantially homogeneous compositions of MSC. In such compositions, the cells having an MSC phenotype are usually at least about 50% of the total number of cells; at least about 75% of the total number of cells; at least about 85% of the total number of cells; at least about 90% of the total number of cells; or more.

In some embodiments, the homogeneous MSC composition is stable in non-differentiating culture conditions, where the proportion of cells in the composition that have an MSC phenotype are maintained over multiple passages. Such cells may be maintained for at least about two passages; at least about five passages; at least about ten passages; or more.

Non-differentiating culture conditions. MSC as described above can be propagated continuously in culture, using culture conditions that promote proliferation without promoting differentiation, using methods known in the art. The cells can be maintained in medium, e.g. DMEM; RPMI; etc. in the presence of fetal bovine serum or serum-free replacement without differentiation. Generally the cells are passaged at about 75 to 95% confluence, using a protease, e.g. trypsin, collagenase, etc.

Differentiating culture conditions. Differentiating cells are obtained by culturing or differentiating MSC in a growth environment that enriches for cells with the desired phenotype, e.g. osteoblasts, adipocytes, etc. The culture may comprise agents that enhance differentiation to a specific lineage.

Osteogenic differentiation may be performed by plating cells and culturing to confluency, then culturing in medium comprising β-glycerol phosphate, ascorbic acid and retinoic acid (see Cowan et al. (2005) Tissue engineering 11, 645-658).

Adipogenic differentiation may be performed by plating cells and culturing to confluency, then culturing in medium comprising dexamethasone, indomethacin, 3-isobutyl-1-methylxanthine (IBMX), and insulin, then maintaining in growth media with 1 insulin.

Myocyte differentiation may be performed by plating cells and culturing to confluency, then culturing in medium comprising horse serum, dexamethasone, and hydrocortisone (see Eun et al. (2004) Stem Cells 22:617-624); or 5-azacytidine (see Fukuda et al. (2001) Artificial Organs 25:187).

Chondrocyte differentiation may be performed by plating cells and culturing to confluency, then culturing in medium comprising dexamethasone, ascorbic acid 2-phosphate, insulin, transferrin, selenous acid, with or without TGF-$β_1$ (see Williams et al. (2003) Tissue Engineering 9(4):679).

Following the differentiation in culture, the culture will usually comprise at least about 25% of the desired differentiated cells; more usually at least about 50% differentiated cells cells; at least about 75% differentiated cells, or more. The cells thus obtained may be used directly, or may be further isolated, e.g. in a negative selection to remove MSCs and other undifferentiated cells. Further enrichment for the desired cell type may be obtained by selection for markers characteristic of the cells, e.g. by flow cytometry, magnetic bead separation, panning, etc., as known in the art.

Constructs for the Detection and Separation of MSC

In one embodiment of the invention, a nucleic acid construct is introduced into a population of cells comprising MSC, where the construct comprises sequences encoding a detectable marker, which marker is operably linked to a transcriptional response element regulated by β-catenin, herein termed a "detection construct". In the presence of nuclear β-catenin, the detectable marker is expressed, and indicates that a cell is an MSC. In this aspect, the method may be used to determine whether a test cell is an MSC. Viable cells expressing the marker can also be sorted, in order to isolate or enrich for MSC.

A variety of vectors are known in the art for the delivery of sequences into a cell, including plasmid vectors, viral vectors, and the like. In a preferred embodiment, the vector is a retroviral or lentiviral vector. For example, see Baum et al., (1996) J Hematother 5(4):323-9; Schwarzenberger et al. (1996) Blood 87:472-478; Nolta et al. (1996) P.N.A.S. 93:2414-2419; and Maze et al. (1996) P.N.A.S. 93:206-210, Mochizuki et al. (1998) J Virol 72(11):8873-83. The use of adenovirus based vectors with hematopoietic cells has also been published, see Ogniben and Haas (1998) *Recent Results Cancer Res* 144:86-92.

The beta-catenin transcriptional response element (TRE) will comprise one or more nucleotide motifs that bind a transcription factor activated by β-catenin. In a preferred embodiment, the transcription factor is LEF/TCF (for a review, see Roose and Clevers (1999) Biochim Biophys Acta 1424(2-3):M23-37, herein incorporated by reference). Transcriptionally inert LEF/Tcf factors become potent transactivators upon interaction with beta-catenin in the nucleus. It may be noted that β-catenin is found in the cytoplasm, but its primary biological effects are seen when it is activated and translocated into the nucleus. Nucleotide elements responsive to this signaling pathway include, for example TBE1 (CCTTTGATT) and TBE2 (GCTTTGATC), which are contained on the human c-MYC promoter Kpnl to Pvull fragment, see He et al. (1998) *Science* 281:1509; LEF/TCF binding motifs, (e.g. CCTTTGATC; or CCTTTGGCC)(Korinek et al. (1997) *Science* 275:1784-1787); LEF-1 binding sites, SEQ ID NO: 1; GCTTTGATCTT (Shtutman et al. (1999) *Proc Natl Acad Sci U S A* 96(10):5522-7), and otherwise as known in the art. There references are herein specifically incorporated by reference for their teaching of sequences responsive to LEF-1/TCF. The complement of these sequences may also be used, e.g. (SEQ ID NO: 2 GATCAAAGGG.

In one embodiment of the invention, the β-catenin responsive TRE comprises one or more, two or more, three or more, etc. of a binding motif sequence (SEQ ID NO: 3 $X^1$ C T T T G Pu T Py; where $X^1$ is G or C, Pu is purine and Py is pyrimidine. In a preferred embodiment the β-catenin responsive TRE comprises one or more, two or more, three or more, etc. of a binding motif sequence that is the complement of SEQ ID NO: 3; 5' Pu A Py C A A A G $X^1$ 3', where $X^1$ is G or C, Pu is purine and Py is pyrimidine.

Operably linked to the β-catenin TRE is a detectable marker. Many such markers are known in the art, for example antibiotic resistance, color change of a substrate, expression of a recombinase, e.g. cre recombinase, FLP recombinase, pSR1 recombinase, etc., which is indirectly detected; expression of luminescence producing proteins, e.g. luciferase, green fluorescent proteins, etc.

In a preferred embodiment of the invention, the marker is a luminescence producing protein, preferably GFP. The native gene encoding this protein has been cloned from the bioluminescent jellyfish *Aequorea victoria* (Morin, J. et al., J Cell Physiol (1972) 77:313-318). The availability of the gene has made it possible to use GFP as a marker for gene expression. GFP itself is a 283 amino acid protein with a molecular weight of 27 kD. It requires no additional proteins from its native source nor does it require substrates or cofactors available only in its native source in order to fluoresce. (Prasher, D. C. et al., Gene (1992) 111:229-233; Yang, F. et al., Nature Biotechnol (1996) 14:1252-1256; Cody, C. W. et al., Biochemistry (1993) 32:1212-1218.) Mutants of the GFP gene have been found useful to enhance expression and to modify excitation and fluorescence. GFP-S65T (wherein serine at 65 is replaced with threonine) may be used, which has a single excitation peak at 490 nm. (Heim, R. et al., Nature (1995) 373:663-664); U.S. Pat. No. 5,625,048. Other mutants have also been disclosed by Delagrade, S. et al., Biotechnology (1995) 13:151-154; Cormack, B. et al., Gene (1996) 173:33-38 and Cramer, A. et al. Nature Biotechnol (1996) 14:315-319. Additional mutants are also disclosed in U.S. Pat. No. 5,625,048. By suitable modification, the spectrum of light emitted by the GFP can be altered. Thus, although the term "GFP" is used in the present application, the proteins included within this definition are not necessarily green in appearance. Various forms of GFP exhibit colors other than green and these, too, are included within the definition of "GFP" and are useful in the methods and materials of the invention. In addition, it is noted that green fluorescent proteins falling within the definition of "GFP" herein have been isolated from other organisms, such as the sea pansy, *Renilla reriformis*. Any suitable and convenient form of the GFP gene can be used in the methods of the invention.

Various techniques known in the art may be used to transfect the target cells, e.g. electroporation, calcium precipitated DNA, fusion, transfection, lipofection and the like. The particular manner in which the DNA is introduced is not critical to the practice of the invention.

Combinations of retroviruses and an appropriate packaging line may be used, where the capsid proteins will be functional for infecting the target cells. Usually, the cells and virus will be incubated for at least about 24 hours in the culture medium. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells.

The sequences at the 5' and 3' termini of the retrovirus are long terminal repeats (LTR). A number of LTR sequences are known in the art and may be used, including the MMLV-LTR; HIV-LTR; AKR-LTR; FIV-LTR; ALV-LTR; etc. Specific sequences may be accessed through public databases. Various modifications of the native LTR sequences are also known. The 5' LTR acts as a strong promoter, driving transcription of the β-catenin gene after integration into a target cell genome. For some uses, however, it is desirable to have a regulatable promoter driving expression. Where such a promoter is included, the promoter function of the LTR will be inactivated. This is accomplished by a deletion of the U3 region in the 3' LTR, including the enhancer repeats and promoter, that is sufficient to inactivate the promoter function. After integration into a target cell genome, there is a rearrangement of the 5' and 3' LTR, resulting in a transcriptionally defective provirus, termed a "self-inactivating vector".

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in hematopoietic cell types, e.g. IL-2 promoter in T cells, immunoglobulin promoter in B cells, etc.

For detecting or selecting stem cells, the detection construct is introduced into a cell or population of cells, suspected of being or comprising stem cells. After introduction of the expression construct, the cells are maintained for a period of time sufficient to express the detectable marker, usually at least about 12 hours and not more than about 2 weeks, and may be from about 1 day to about 1 week.

Genetic constructs may be removed from the target cells after expansion. This can be accomplished by the use of a transient vector system, or by including a heterologous recombination site that flanks the beta-catenin coding sequence. In this manner, after expansion the construct can be removed prior to use of the expanded cell population. Preferably a detectable marker, e.g. green fluorescent protein, luciferase, cell surface proteins suitable for antibody selection methods, etc. is included in the expression vector, such that after deletion of the construct the cells can be readily isolated that lack the exogenous beta-catenin. The term "heterologous recombination site" is meant to encompass any introduced genetic sequence that facilitates site-specific recombination. In general, such sites facilitate recombination by interaction of a specific enzyme with two such sites. Exemplary heterologous recombination sites include, but are not necessarily limited to, lox sequences with recombination mediated by Cre enzyme; frt sequences (Golic et al. (1989) *Cell* 59:499-509; O'Gorman et al. (1991) *Science* 251:1351-5; recombination mediated by the FLP recombinase), the recognition sequences for the pSR1 recombinase of *Zygosaccharomyces rouxii* (Matsuzaki et al. (1990) *J. Bacteriol.* 172: 610-8), and the like.

Expression vectors that provide for the transient expression in mammalian cells may be used. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient short term expansion of cells, but do not affect the long term genotype of the cell.

The immortalizing construct, which provides for modulation of the ability of a cell to proliferate, is introduced into the hematopoietic cells by any of a variety of different methods. Preferably the hematopoietic cells are progenitor or stem cells, including myeloid progenitor cells, hematopoietic stem cells, lymphoid progenitor cells, multilineage progenitors, and the like. For a review of the lineages of hematopoietic stem cells and progenitors, see Wagers et al. (2002) Gene Ther. 9(10):606-12; Park et al. (2002) Blood 99(2):488-98; and Weissman et al. (2001) Annu Rev Cell Dev Biol 17:387-403, herein each incorporated by reference.

The methods used for introduction of the β-catenin include "ex vivo" transfection of a target cell, which target cell may be the target cell, e.g. a progenitor cell; or a stem cell that gives rise to the target cell. Methods of interest include the use of naked DNA, DNA-liposome conjugates, retroviral vectors, lentiviral vectors, etc. followed by culture of the cells in vitro, or implantation of the transformed cells into the host mammal, such as a mouse or a human.

Selection Methods

The expression of the detectable marker, where the marker is a fluorescent protein, can be monitored by flow cytometry, where lasers detect the quantitative levels of fluorophore. Flow cytometry, or FACS, can also be used to separate cell populations based on the intensity of fluorescence, as well as other parameters such as cell size and light scatter. Although the absolute level of staining may differ, the data can be normalized to a control.

In addition to expression of the β-catenin-regulated marker gene, the cells may be co-stained with antibodies specific for markers of interest, e.g. thy-1 (CD-90); CD105; CD73; CD29; CD44; CD45; CD34, and the like, as known in the art.

The cells of interest may be separated from a complex mixture of cells by techniques that enrich for cells having the above characteristics. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for MSC activity are achieved in this manner. The subject population may be at or about 50% or more of the cell composition, and preferably be at or about 75% or more of the cell composition, and may be 90% or more. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium.

The enriched cell population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

In some embodiments, the selected cells are maintained in culture for at least one passage, usually at least about two passages; at least about three passages; or more, and not more than about 10 passages, usually not more than about seven passages. Following such culture, the cells are sorted for expression of the detectable marker as described above. It has been found that such cultured and resorted cells have an unexpectedly stable maintenance of the MSC phenotype.

The stem cells isolated by the methods of the invention, and cells and animals generated by introduction of an immortalizing construct find use in compound screening, for the identification of genes expressed in stem cells, for therapies utilizing stem cells, and the like.

Compound Screening

The cells are also useful for in vitro assays and screening to detect factors that are active on differentiating mesenchymal cells. Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, viruses, etc. the subject cells, usually a culture comprising the subject cells, is contacted with the agent of interest, and the effect of the agent assessed by monitoring output parameters, such as expression of markers, cell viability, and the like. The cells may be freshly isolated, cultured, genetically altered as described above, or the like. The cells may be environmentally induced variants of clonal cultures: e.g. split into independent cultures and grown under distinct conditions, for example with or without virus; in the presence or absence of other cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents, such as viruses, candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 µl to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51(3):313-24, for examples.

Genetic Screening

The substantially homogeneous compositions of MSC are also useful as a source of MSC specific genetic material, particularly mRNA transcripts. A nucleic acid derived from an mRNA transcript refers to a nucleic acid for whose synthesis the mRNA transcript, or a subsequence thereof, has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample.

A number of methods are available for analyzing nucleic acids for the presence of a specific sequence, e.g. upregulated or downregulated expression. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. *Molecular Cloning: A Laboratory Manual*, CSH Press 1989, pp. 14.2-14.33.

A detectable label may be included in an amplification reaction. Suitable labels include fluorochromes, e.g. ALEXA dyes (available from Molecular Probes, Inc.); fluorescein isothiocyanate (FITC), rhodamine, Texas Red, phycoerythrin, allophycocyanin, 6-carboxyfluorescein(6-FAM), 2,7-dimethoxy-4,5-dichloro-6-carboxyfluorescein (JOE),6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified, labeled, cloned fragment, etc. is analyzed by one of a number of methods known in the art. Probes may be hybridized to northern or dot blots, or liquid hybridization reactions performed. The nucleic acid may be sequenced by dideoxy or other methods, and the sequence of bases compared to a wild-type sequence. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Fractionation is performed by gel or capillary electrophoresis, particularly acrylamide or agarose gels.

In situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the walls of a microtiter well) and then permeabilizing the cells with an appropriate permeabilizing solution. A solution containing labeled probes is then contacted with the cells and the probes allowed to hybridize. Excess probe is digested, washed away and the amount of hybridized probe measured. This approach is described in greater detail by Nucleic Acid Hybridization: A Practical Approach (Hames, et al., eds., 1987).

A variety of so-called "real time amplification" methods or "real time quantitative PCR" methods can also be utilized to determine the quantity of mRNA present in a sample. Such methods involve measuring the amount of amplification product formed during an amplification process. Fluorogenic nuclease assays are one specific example of a real time quantitation method that can be used to detect and quantitate transcripts. In general such assays continuously measure PCR product accumulation using a dual-labeled fluorogenic oligonucleotide probe—an approach frequently referred to in the literature simply as the "TaqMan" method. Additional details regarding the theory and operation of fluorogenic methods for making real time determinations of the concentration of amplification products are described, for example, in U.S. Pat. No. 5,210,015 to Gelfand, 5,538,848 to Livak, et al., and 5,863,736 to Haaland, each of which is incorporated by reference in its entirety.

Screening for expression of β-catenin may be based on the functional or antigenic characteristics of the protein, including the nuclear localization of the protein. Various immunoassays designed to detect polymorphisms may be used in screening. Detection may utilize staining of cells or histological sections, performed in accordance with conventional methods, using antibodies or other specific binding members that specifically bind to β-catenin. The antibodies or other specific binding members of interest are added to a cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art.

For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

Methods of Transplantation

The substantially homogeneous mesenchymal stem cell compositions of the invention find use in the treatment of degenerative diseases, and the immunomodulation of transplantation, and may be delivered as progenitor cells; as differentiated progeny thereof, e.g. after commitment to a lineage of interest; and/or as a means of delivering gene products to the affected area.

A cell transplant, as used herein, is the transplantation of one or more cells into a recipient body, usually for the purpose of augmenting function of an organ or tissue in the recipient. As used herein, a recipient is an individual to whom tissue or cells from another individual (donor), commonly of the same species, has been transferred. The graft recipient and donor are generally mammals, preferably human. Laboratory animals, such as rodents, e.g. mice, rats, etc. are of interest for drug screening, elucidation of developmental pathways, etc.

For the purposes of the invention, the cells may be allogeneic, autologous, or xenogeneic with respect to the recipient. MSC are at least partially protected from immune rejection, and therefore a perfect match of histocompatibility antigens is not required for allogeneic transplantation. Usually at least one HLA match is provided, more usually two matches, three matches, four matches, five matches, or more. The number of cells to be transplanted will vary with the specific treatment that is desired, the size of the recipient, and the like. In general, for a human, at least about $10^4$ cells/KG will be administered; at least about $10^5$; at least about $10^6$; at least about $10^7$; or more.

Where the transplantation is intended for the treatment of degenerative disease, e.g. osteogenesis imperfecta; repair of mesenchymal tissues; etc., the cells are administered in a manner that permits them to graft or migrate to the intended tissue site and reconstitute or regenerate the functionally deficient area. MSCs find use for engineering cartilage, growth plate, bone and tendon/ligament as well as the clinical trial of autologous chondrocyte implantation (see, for example, Hui et al. (2005) Ann Acad Med Singapore).

Genetically engineered mesenchymal stem cells can be used to target gene products to sites of degeneration. These gene products can include survival-promoting factors to rescue bone or cartilage, factors that can act in an autocrine manner to promote survival and differentiation of grafted cells. Therapy using MSC engineered to synthesize a growth factor or a combination of growth factors can not only ensure sustained delivery of factors, but may also reconstruct damaged tissue. For example, it has been shown that human mesenchymal stem cells ectopically expressing full-length dystrophin can complement Duchenne muscular dystrophy myotubes by cell fusion (Goncalves et al. (2006) Hum Mol Genet. 15(2):213-21).

Compositions and methods are provided for increasing the survival of cells during the process of transplantation. Cells to be transplanted are administered together with the substantially homogeneous mesenchymal stem cell compositions of the invention. MSC have immunomodulatory effects, enhance hematopoietic engraftment in recipients of autologous and allogeneic grafts; inhibit T-cell proliferation in mixed lymphocyte cultures, prolong skin allograft survival, and can decrease graft-versus-host disease (GVHD) when co-transplanted with hematopoietic stem cells. MSCs induce their immunosuppressive effect via a soluble factor. In allogeneic stem cell transplantation, MSCs are used for hematopoiesis enhancement, as GVHD prophylaxis, and for the treatment of severe acute GVHD. They are also of use in the treatment of organ transplant rejection and in autoimmune inflammatory bowel disorders where immunomodulation and tissue repair are needed (see Le Blanc and Ringden (2005) Biol Blood Marrow Transplant. 11(5):321-34). The cells of the invention may be administered before transplantation, at the same time, or following transplantation.

The compositions of the invention provide for increased survival of transplanted cells after they are transferred to a recipient animal. In experimental systems, survival of cells may be measured after short periods of time, e.g. after at least about three to about seven days. When measured over such a time period, the methods of the invention provide for an increase in cell survival of at least about 5-fold, at least about 10-fold, at least about 20-fold, at least about 50-fold, at least about 100-fold, or more, relative to transplantation in the absence of the MSCs.

Cells of interest for transplantation include, without limitation, cardiomyocytes and progenitors thereof; neural progenitor cells, e.g. for the regeneration of neurons, or retina, and the like; pancreatic islet cells, particularly pancreatic β-cells; hematopoietic stem and progenitor cells; muscle satellite cells; endothelial cells or progenitors thereof; and the like. Tissues of interest include liver tissue, kidney tissue, heart tissue, lung tissues, skin tissue, brain tissue; spinal cord tissue; pancreatic islets; retinal tissue; and the like.

In the methods of the invention, cells to be transplanted are transferred to a recipient in any physiologically acceptable excipient comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996. Choice of the cellular excipient and any accompanying elements of the composition will be adapted in accordance with the route and device used for administration. The cells may be introduced by injection, catheter, or the like. The cells may be frozen at liquid nitrogen temperatures and stored for long periods of time, being capable of use on thawing. If frozen, the cells may be stored in a 10% DMSO, 50% FCS, 40% RPMI 1640 medium.

Conditions of Interest for Therapy

In one embodiment of the invention, the MSC are used in the treatment of osteogenesis imperfecta, or "brittle-bone" disease, which is a defect in the production of collagen resulting in repeated fractures with minor trauma. Collagen, of which there are at least 10 identifiable subtypes, is found in the connective tissues of the body and makes up a large portion of the bones and cartilage. For a person with OI, either the amount of collagen being produced is too little, or the quality being produced is poor. It is estimated that OI affects between 20,000 and 50,000 people in the United States. OI is a genetic disease. The inheritance pattern is usually autosomal dominant.

There are four types of OI. Type I is the most common and mildest form of OI. It is autosomal dominant in its inheritance, but it may also result from a spontaneous mutation.

People with Type I OI average nearly 40 fractures before puberty; however, they experience only a few fractures after puberty. The collagen in Type I OI is normal, but the amount produced is less than normal. Affecting approximately 10 percent of people with OI, Type II is the most severe form of this disease. The result of a spontaneous gene mutation, the collagen in Type II OI is improperly formed. The bones of people with Type II OI are extremely fragile and often have severe deformities. Type II OI frequently causes death at or shortly after birth. Type III OI affects 20 percent of the people who have OI. The collagen in Type III OI is improperly formed. The severity of Type IV falls between Type I and Type III. It is inherited in an autosomal dominant manner, although it can also result from a spontaneous mutation. Fractures are most common in OI Type IV before puberty. The exception to this is in women, who after menopause experience a resurgence in the number of fractures.

A doctor can often make the diagnosis of OI after a thorough physical examination using the above symptoms as guides, as well as a review of a family's medical history. However, sometimes it is necessary to perform laboratory tests to test the collagen or genetic pattern of the disease. A cure for OI has yet to be found. Because of this, treatment for the disease focuses on managing the symptoms, preventing complications, and developing and maintaining bone mass and muscle strength.

Kits

The formulations of the invention are optionally packaged in a suitable container with written instructions for a desired purpose. Such formulations may comprise a vector, in a form suitable for combining with cells prior to selection. Such a composition may further comprise suitable buffers and/or excipients appropriate for culture.

For further elaboration of general techniques useful in the practice of this invention, the practitioner can refer to standard textbooks and reviews in cell biology, tissue culture, and embryology. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Other features and advantages of the invention will be apparent from the description of the preferred embodiments, and from the claims. The following examples are offered by way of illustration and not by way of limitation.

EXPERIMENTAL

Example 1

We sought to overcome the difficulties in studying MSC biology by employing a novel approach that would allow isolation of cell populations based upon a functional responsiveness to canonical Wnt signaling through β-catenin. Progenitor cells within a heterogeneous population of MSC may have unique biological properties conferred by activation of the canonical Wnt signaling pathway. Specifically, cells in which canonical Wnt signaling is active may represent a unique, highly proliferative sub-population of cells with multi-potent differentiation capabilities. The objective of these studies was to enrich for stem or progenitor cells from the mixed population of MSC.

Methods.

Harvest and Culture of MSCs: MSCs were harvested as previously described (Cowan et al. (2004) *Nature biotechnology* 22, 560-567). Briefly, inguinal fat pads were harvested from 3-4 week old FVB/n mice (Charles River Laboratories). Animals were housed and cared for in accordance with all regulations set forth by Administrative Panel of Laboratory and Animal Care at Stanford University. The adipose tissue was minced and then digested with 0.075% collagenase type II for 30 minutes at 37 degrees. After digestion the collagenase was neutralized with DMEM with 10% FBS. The cells were centrifuged at 1000 rpm for 5 minutes. The cell pellet was resuspended in DMEM with 10% FBS and placed in culture. After 12 hours the non-adherent cells were washed away. Cells were maintained in DMEM with 10% FBS. The media was changed every three days. At 90% confluence the cells were passaged with 0.05% Trypsin/0.53 mM EDTA.

Vector production: 293T cells were plated at a concentration of $4-5 \times 10^6$ per 10 cm dish. After 24 hours the cells were transfected with the transfer vector plasmids pRRLsin-18.PPT.PGK.GFP.pre or pRRL.sin-18.PPT.TOP-GFP.pre, the VSV G envelope-encoding plasmid pMD.G-VSV, and the packaging plasmid CMVΔR8.74. The supernatant was harvested, ultracentrifuged, and the vector pellet was resuspended in a small volume of PBS/0.1% BSA. Vector titer was determined by adding serial dilutions to Jurkat cells which have constitutively active Wnt signaling, and determining the proportion of GFP expressing cells by flow cytometric analysis 72 hours later using the Vantage or Vantage SE/DiVa cell sorting machines (Becton Dickinson) at the Stanford University shared FACS facility.

Transduction with Lentivirus: After 24-48 hours in culture the non-adherent cells were washed away and remaining AMSCs were transduced with equivalent titers of either TOP-GFP lentivirus, PGK-GFP lentivirus, or treated with an equivalent volume of PBS. 72 hours after addition of the virus cells were trypsinized with 0.05% trypsin/0.53 mM EDTA and resuspended in HBSS with 2% FBS and propidium iodide. The transduction efficiency was estimated by analyzing the GFP expressing cells that had been transduced with the PGK-GFP lentivirus. The percentage of TOP-GFP positive cells was similarly assessed by analyzing cells transduced with TOP-GFP lentivirus. All analysis and cell sorting was performed at the Stanford shared FACS facility using the FACS machines described above.

Cell Growth Assay: Cell growth was assessed by both cell counting and cell number extrapolation as well as by a calorimetric BRDU incorporation ELISA assay (Roche). Cells were plated at a concentration of 1000 cells per well in each well of a 96 well plate. Each condition was tested in triplicate or quadruplicate.

Osteogenic Differentiation: Osteogenic differentiation was performed by plating cells at $2\times10^4$ cells per well in a 12 well plate. Cells were grown until confluent and then treated with DMEM with 10% FBS, 1% penicillin/streptomycin, 0.01 M β-glycerol phosphate, 100 μg/ml ascorbic acid and 2.5 μM retinoic acid (Sigma) as previously described (Cowan et al. (2005) Tissue engineering 11, 645-658).

Alkaline Phosphatase Staining: Alkaline phosphatase staining was performed after 5 days in differentiation media by fixing the cells with a mixture of citrate working solution (Sigma) and acetone. The cells were then stained for alkaline phosphatase by using a mixture of Fast Violet B and Napthol AS-MX Phosphate Alkaline Solution (Sigma 159-6 and 85-5). Alkaline phosphatase activity was quantified using the Sigma Diagnostics procedure 104, and was normalized to protein content using BCA protein assay (Pierce).

Alizarin Red Staining and Quantification: Alizarin Red staining was performed to assess extracellular matrix mineralization after 14-21 days in differentiation media. This was performed by fixing the cells with 100% ethanol for 15 minutes, and then staining with 0.2% Alizarin Red solution with a pH of 6.36-6.4 at room temperature for 1 hour. Alizarin Red was quantified using a solution of 20% methanol and 10% acetic acid in water. After 15 minutes liquid was transferred to cuvettes and quantity of Alizarin Red was read on the spectrophotometer at a wavelength of 450. The quantity was normalized to protein content of cells in parallel plates as quantified using a BCA protein assay (Pierce).

Adipogenic Differentiation and Oil Red O Staining: Adipogenic differentiation was performed by plating cells at $2\times10^4$ cells per well in a 12 well plates and allowing cells to grow to confluence prior to differentiation. To induce adipogenesis cells were treated with DMEM with 10% FBS, 1% penicillin/streptomycin, $1\times10^{-6}$ M dexamethasone, $2\times10^{-4}$ M indomethacin, $5\times10^{-4}$ M 3-isobutyl-1-methylxanthine (IBMX), and insulin 10 mg/mL for 4 days. The cells were then maintained in growth media with 1 mg/mL of insulin. After a total of 10-12 days of differentiation, cells were fixed with 10% buffered neutral formalin for 30 minutes, and then stained with 0.18% Oil Red O in isopropyl alcohol for 1 hour.

Wnt Conditioned Media Production: L cells engineered to over-express Wnt 3a, Wnt 5a, and without Wnt protein over-expression were plated at a density of $4\times10^5$ cells in 12-well dishes. Cells were cultured in DMEM with 10% FBS and 1% penicillin/streptomycin. Media was collected 24, 48, and 72 hours after plating and centrifuged for 10 minutes at 2000 rpm. The media was pooled. Conditioned media was diluted to 50% with DMEM with 10% FBS.

Blocking with dnTCF: Lentivirus expressing dominant negative (dn)TCF4 (REF. van de Wetering et al, Cell 111: 241) under the control of the constitutive PGK promoter was generated as described above. Cells that had been transduced with the TOP-GFP lentivirus and resorted at passage 4 were cultured in the presence of PGK-dnTCF4 lentivirus for 72 hours. Control cells were mock transduced with PBS.

Results

To test the hypothesis that cells with activated canonical Wnt signaling represent a unique subpopulation of primary culture AMSC, we tested a standard AMSC preparation for the presence of cells responsive to canonical Wnt signaling through β-catenin. We utilized a lentiviral vector containing 3 copies of the consensus TCF/LEF binding motif and a minimal promoter driving expression of the marker gene GFP (TOP-GFP). Cells transduced with this vector will only express GFP when β-catenin is translocated to the nucleus, where it will bind to TCF/LEF transcription factors and activate GFP expression. Thus GFP positive cells represent cells in which canonical Wnt signaling is occurring. In initial experiments we determined that the transduction efficiency of AMSC ranged from 94-99% as assessed by the percentage of cells that were GFP positive after transduction with a control lentivirus containing a constitutive promoter, PGK, driving GFP expression (PGK-GFP). Subsequently, primary cultures of un-passaged AMSC were transduced with an equivalent titer of the lentiviral vector TOP-GFP. After this initial plating and transduction we found that 2.75±1.3% of cells were GFP positive (FIG. 1). The β-catenin responsive (GFP$^+$) and β-catenin unresponsive (GFP$^-$) cells were separated by FACS and cultured separately. At passage four, 51.8±11.6% of the GFP$^+$-derived cells remained GFP$^+$ (FIG. 1), while at passage eight, only 2.1±1.23% of the GFP$^+$-derived cells remained GFP$^+$. This percentage of cells was maintained through subsequent passages (FIG. 1). The initially GFP$^-$ cells remained GFP-through all passages tested (FIG. 1).

At early passages (P1-P7) the GFP$^+$ and GFP– cells demonstrated similar rates of growth as indicated by BRDU incorporation (data not shown) and cell doubling times. At P1 the cell doubling times of the both the GFP$^+$ and GFP$^-$ cells were very similar (1.75±0.15 days for GFP$^+$ cells and 1.48±0.01 days for GFP$^-$ cells). After eight passages the proliferation of the GFP$^+$ derived cells became greater than that of the GFP$^-$ derived cells (FIG. 2). At P8 the cell doubling time of the GFP$^+$-derived cells had increased to 3.51±0.05 days while the doubling time of the GFP$^-$ cells had increased to 6.04±0.03 days (FIG. 2). After 102 days in culture an even greater difference in proliferation was seen. The GFP$^+$-derived cells were at passage 20 and their cell doubling time was 3.53±0.3 days, while the GFP$^-$ derived cells were at passage fifteen and their cell doubling time had increased to 9.1±0.8 days (FIG. 2). These data are indicative of the functional differences in proliferative rates we observed between cells with nuclear β-catenin (GFP$^+$) and those without evidence of β-catenin signaling (GFP$^-$).

Figure 3:
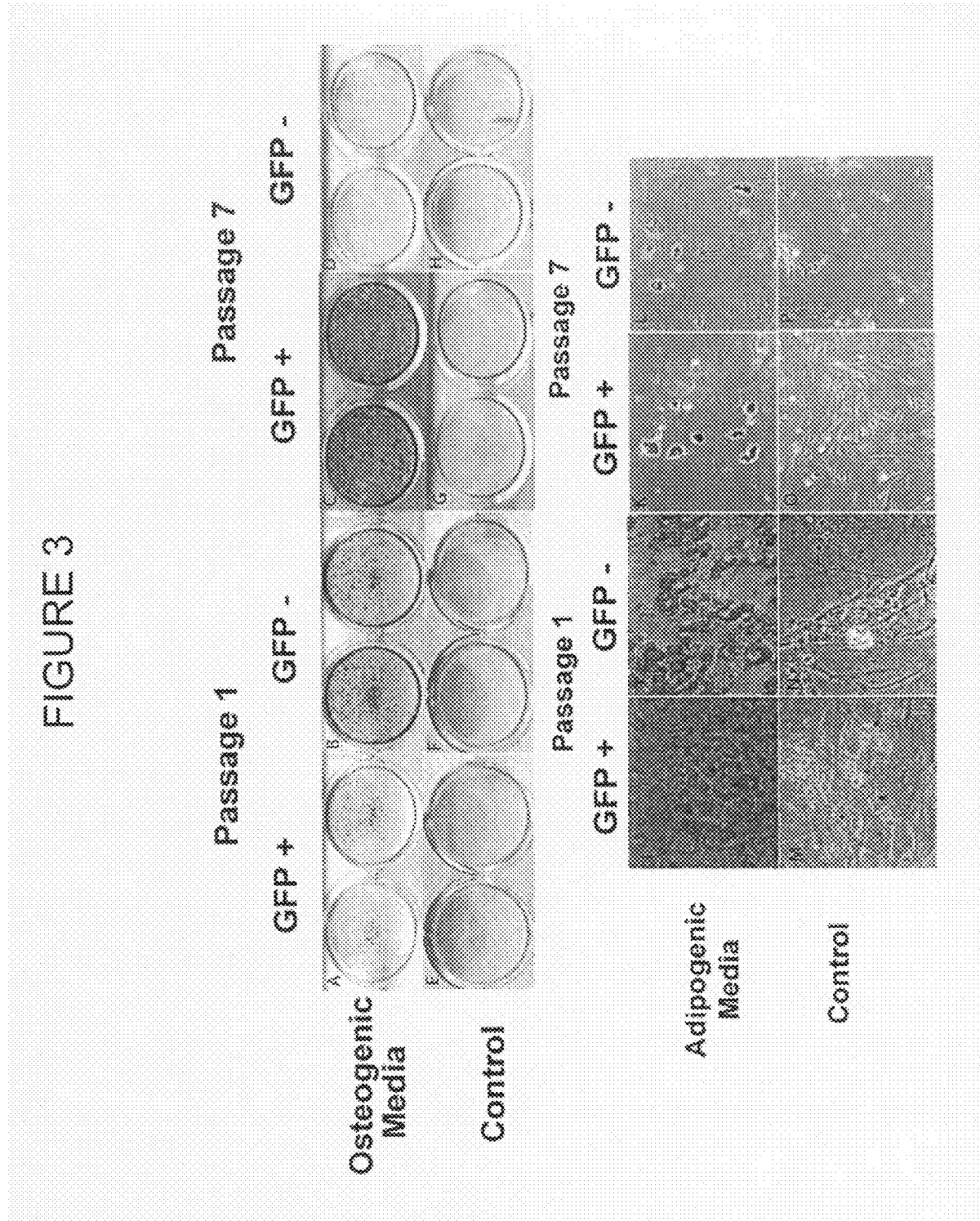
FIG. 3A-P. Alizarin Red staining of sorted MSCs. At passage one both the GFP+ and GFP− cells stained with Alizarin Red when cultured in osteogenic media (A,B). At passage seven only the GFP+ cells stained with Alizarin in osteogenic media (C,D). Cells in control media did not stain with Alizarin Red (E-H). Oil Red O staining of sorted MSCs. Both the GFP+ and GFP− cells stained with Oil Red O at both passage one and seven (I-L). Cells cultured in control media did not stain with Oil Red O (M-P).

In order to determine the differentiation potential of the two AMSC cell populations, we exposed both GFP$^+$ and GFP$^-$ populations to in vitro conditions for osteogenic and adipogenic differentiation. We chose to study differentiation of these two lineages because it has previously been shown that in MSC differentiation and bone remodeling, an increase in adipogenic differentiation results in a concomitant decrease in osteogenic potential, and vice versa. At passage one, both the GFP$^+$ and GFP$^-$ cells underwent osteogenic and adipogenic differentiation as indicated by alizarin red and Oil Red O staining respectively (FIG. 3). At passages seven and twelve, the GFP$^+$-derived cells maintained the ability to undergo osteogenic and adipogenic differentiation, whereas the GFP$^-$ population lost osteogenic potential (negative alizarin red staining) (FIG. 3). These findings demonstrate that in addition to maintaining greater proliferative rates, the cells demonstrating canonical Wnt activation maintained bi-potent differentiation capacity at later passage than their non-activated counter-parts.

Figure 4:
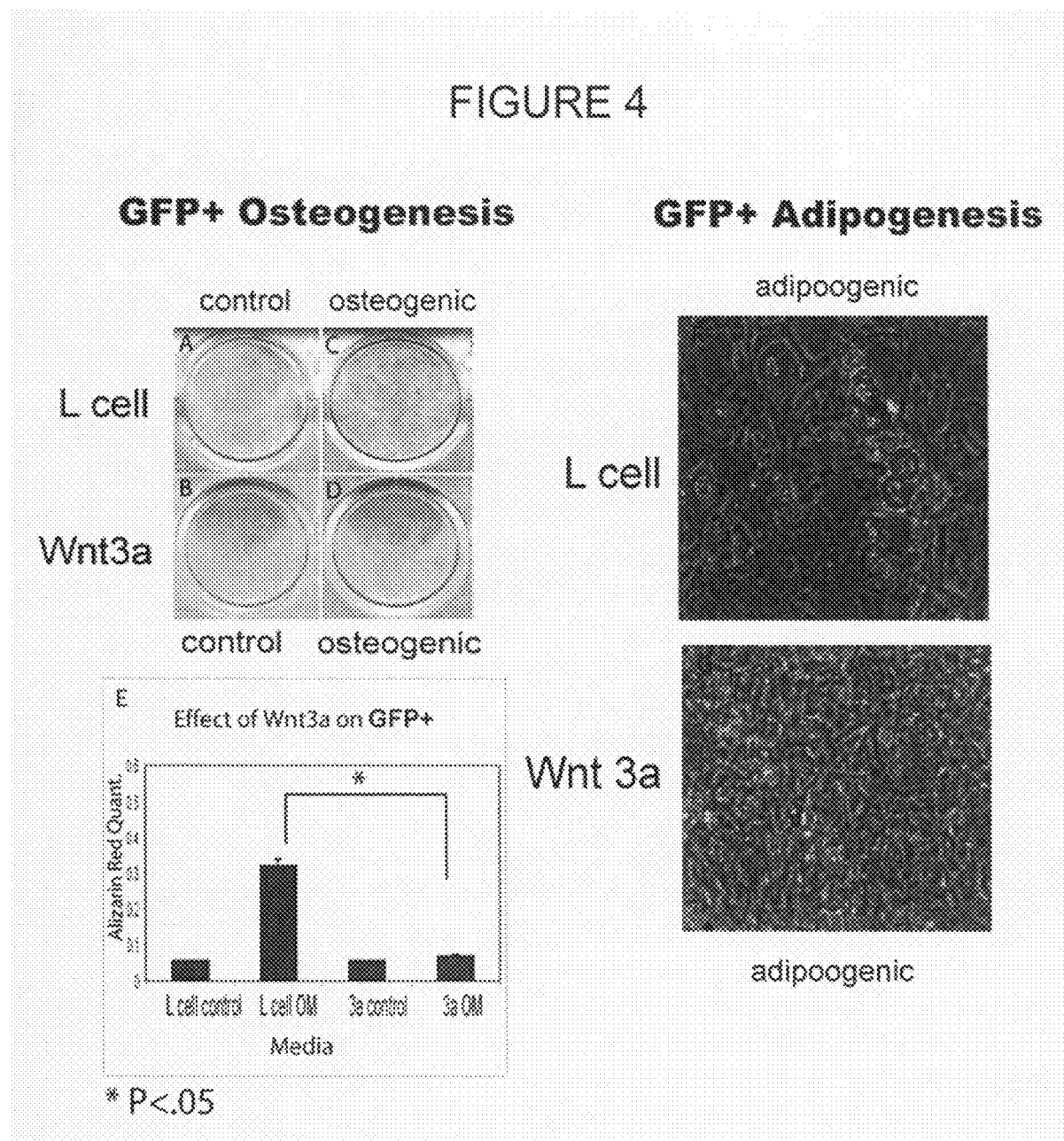
FIG. 4A-4G. Alizarin Red and Oil Red O staining of MSCs cultured in exogenous Wnt3a. GFP+ MSCs cultured in control L cell or Wnt3a conditioned media did not stain with Alizarin Red (A,B). GFP+ MSCs cultured in osteogenic L cell media stained with Alizarin Red (C). Application of Wnt3a media to GFP+ cells in osteogenic media resulted in inhibition of Alizarin Red staining (D). Wnt3a inhibited the increase in Alizarin Red quantity seen in osteogenic media (p<0.001) (E). GFP+ stained with Oil Red O when cultured in adipogenic conditions with L cell media (F). Wnt 3a inhibited Oil Red O staining the GFP+ cells (G).

In order to further test the effect of exogenous Wnt signaling on the GFP$^+$ subset of cells, they were cultured in Wnt conditioned media. After AMSC harvest, transduction with TOP-GFP lentivirus, and sorting, passage 1 GFP$^+$ cells were then grown in either Wnt 3a or Wnt5a conditioned media. The Wnt3a protein, which has previously been shown to signal via β-catenin and the canonical pathway, did not affect cell growth in the GFP$^+$ cell population, as assessed by cell number and BRDU incorporation. However, Wnt 3a conditioned media inhibited osteogenic differentiation in GFP$^+$ cells as seen by Alizarin red staining and quantification (FIG. 4). Wnt3a conditioned media had no effect on the osteogenic differentiation of the GFP$^-$ cells. Additionally, Wnt3a conditioned media inhibited adipogenic differentiation in the GFP+ cells as indicated by Oil Red O staining (FIG. 4). These findings are consistent with the previously described antagonistic role of canonical Wnt proteins on cell differentiation.

Figure 5:
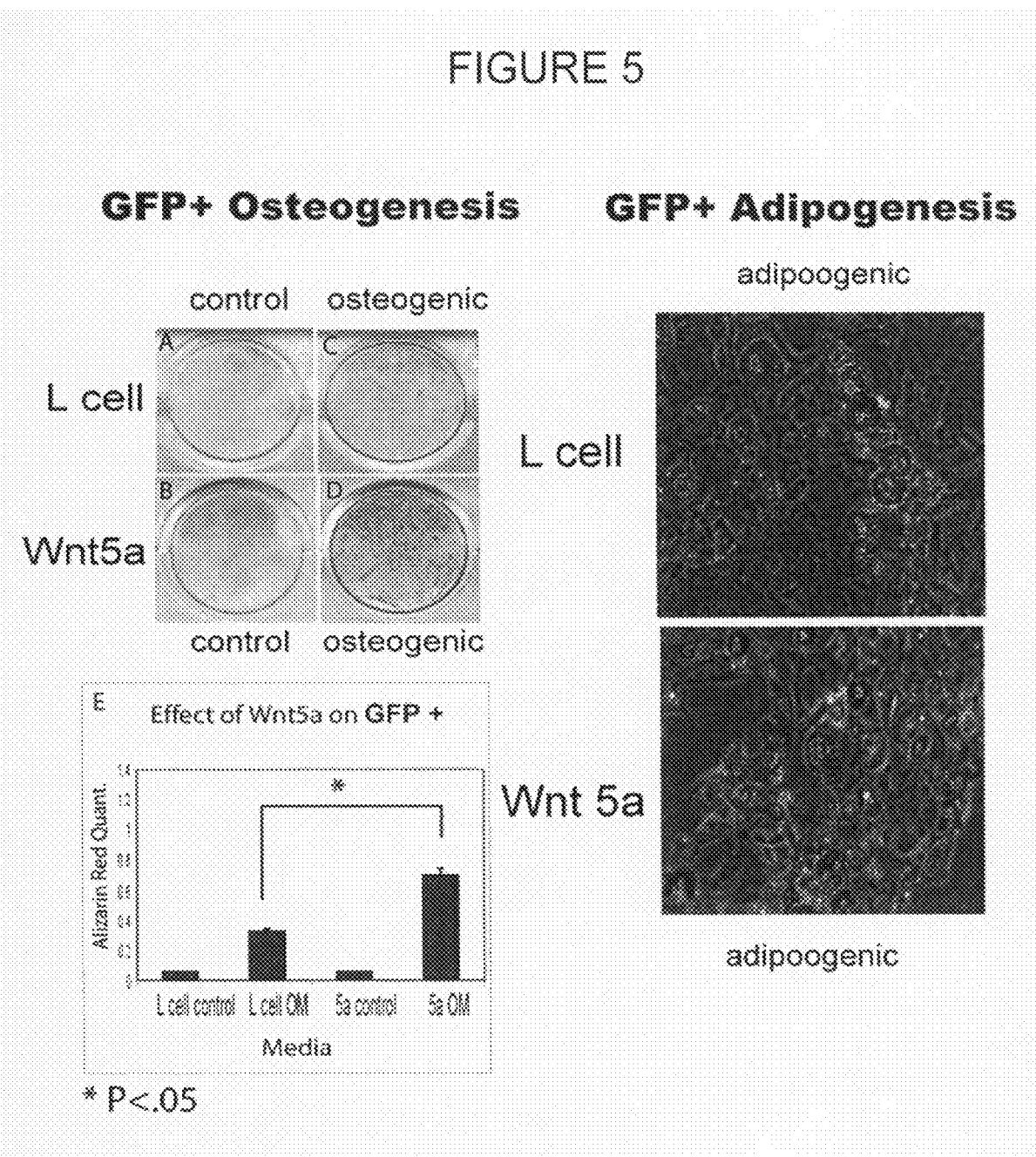
FIG. 5A-5G. Alizarin Red and Oil Red O staining of MSCs cultured in exogenous Wnt5a. GFP+ cells cultured in control media with L cell media or Wnt5a media did not stain with Alizarin Red (A,C). GFP+ cells cultured in osteogenic media with L cell and Wnt5a conditioned media stained with Alizarin Red, but those that had Wnt5a had enhanced staining (B,D). Alizarin Red quantification showed increased quantity of staining of GFP+ cells cultured with Wnt5a (E). The GFP+ cells stained with Oil Red O when cultured in adipogenic conditions with L cell media and Wnt 5a conditioned media indicating that Wnt5a did not impact adipogenesis(F,G).

We next tested the GFP$^+$ cell population's response to the non-canonical Wnt5a protein. Non-canonical Wnts signal through a non β-catenin mediated mechanism. They bind Frizzled proteins, activate heterotrimeric G proteins, and increase intracellular calcium thorough protein kinse C dependant mechanisms. Wnt5a conditioned media was utilized in established cultures along with osteogenic media. Wnt5a induced osteogenic differentiation in both the GFP$^+$ and GFP− cells (FIG. 5). Wnt5a conditioned media did not have an effect on adipogenic differentiation in the GFP$^+$ cells (FIG. 5).

Since we had previously observed that the percent of GFP$^+$ cells within the GFP$^+$-derived cultures diminished with serial passage, we undertook resorting experiments in order to further compare the biological properties of the GFP$^+$ and GFP− populations, and to rule out contamination of the GFP$^-$ cells by the small percentage of cells that remained untransduced by lentivirus. AMSCs were transduced with the TOP-GFP lentiviral construct. The cells were separated into GFP$^+$ and GFP− populations and cultured as described previously. At passage four the GFP$^+$-derived cells were resorted into GFP positive and negative populations. At this time, 51.8±11.6% of cells from the original sorted GFP$^+$ population remained GFP positive.

Figure 6:
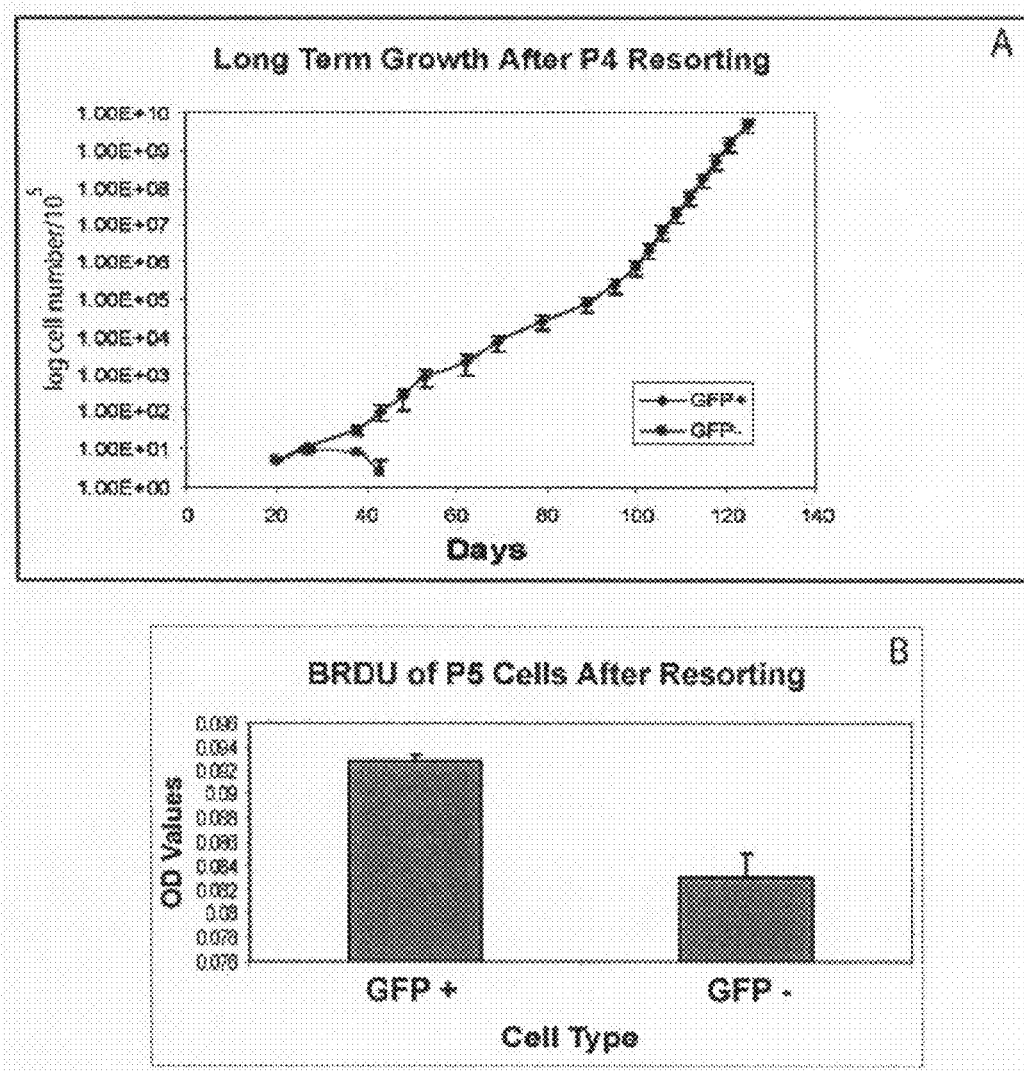
FIG. 6A-6B. BRDU of P5 cells after resorting. The GFP+ cells had significantly (P=0.002) higher BRDU incorporation than GFP− cells.
Figure 7:
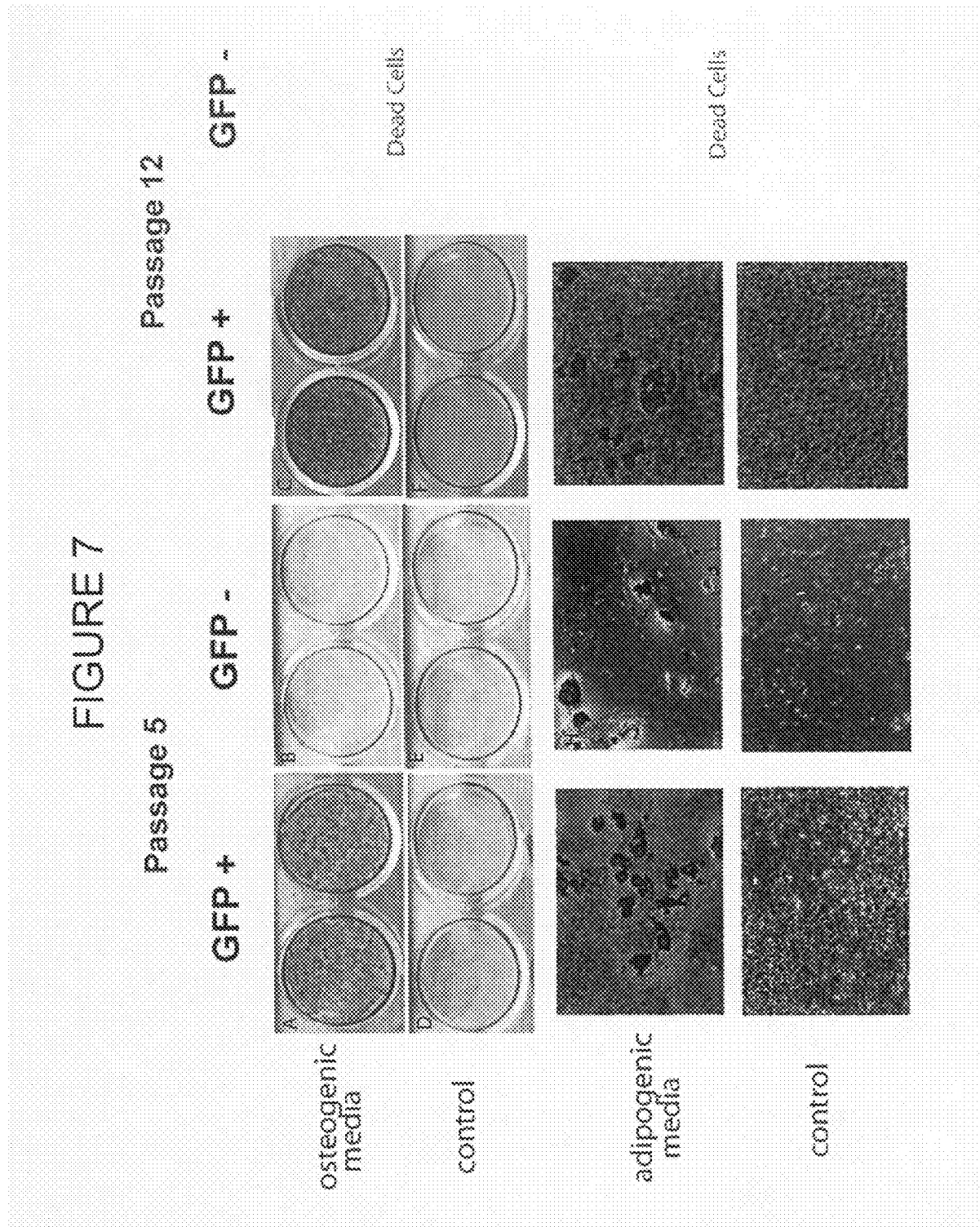
FIG. 7A-7L. Osteogenic and adipogenic differentiation of re-sorted cells. At passages 5 and 12 the resorted GFP+ cells had Alizarin Red staining after culture in osteogenic media (A,C). The passage 5 GFP− cells did not stain with Alizarin Red when cultured in osteogenic media (B). Passage 5 GFP+ and − cells, and passage 12 GFP+ cells stained with Oil Red O when cultured in adipogenic media (G-I). Neither GFP+ or − cells stained with Alizarin Red or Oil Red O when cultured in control media (D-F, J-L). GFP− cells dies at passage 6, therefore could not be stained at passage 12.

The two resorted GFP$^+$ and GFP− populations (each now derived from the originally GFP+ population) were plated and cultured separately. This approach ensured that all of the GFP− cells had been transduced, and were truly unresponsive to TCF/LEF signaling. At passage 5, after this resorting, the GFP$^+$-derived cells had higher rates of cells growth and BRDU incorporation than the GFP− cells (FIG. 6). The GFP$^+$ cells also showed a markedly increased proliferative capacity compared to the GFP− cells. This was indicated by their rapid in vitro growth of the GFP$^+$ cells as compared to the cell death two passages after resorting of the GFP− cells (FIG. 6). At passage 5 the resorted GFP$^+$-derived cells underwent robust osteogenic differentiation as indicated by alizarin red staining, while the GFP− cells did not undergo osteogenic differentiation (FIG. 7), reiterating the result found with the initial sorted cells. At passage 5 both GFP$^+$ and GFP− cells underwent adipogenic differentiation as indicated by Oil Red O staining (FIG. 7). By passage 7 all of the GFP− cells had died. At P12, however the GFP$^+$ cells continued to proliferate and maintained the ability to undergo osteogenic and adipogenic differentiation (FIG. 7).

Figure 8:
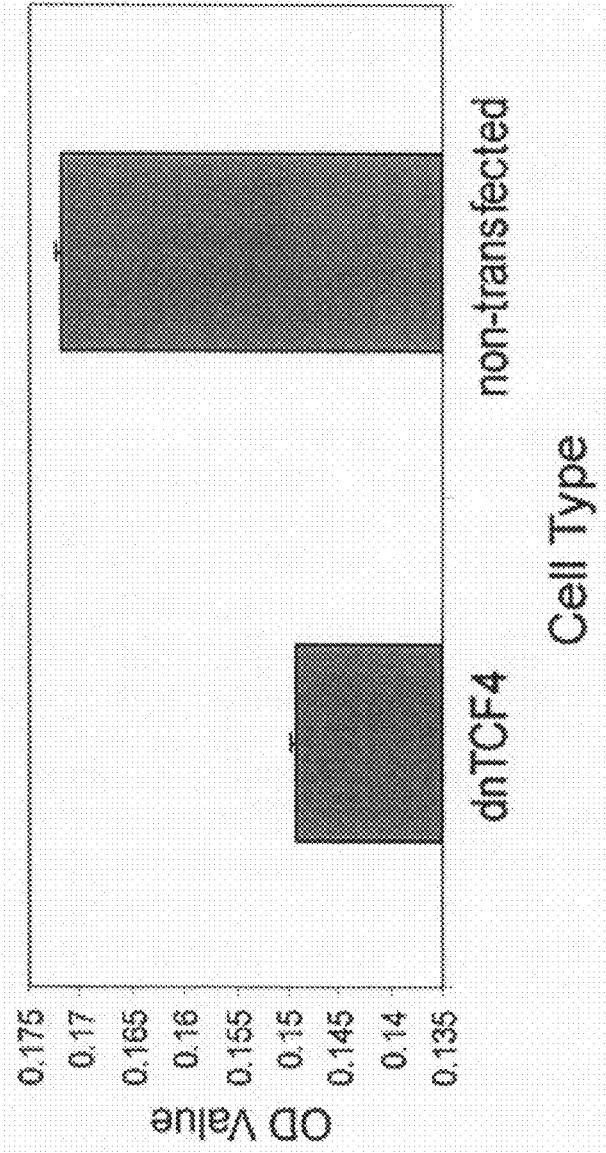
FIG. 8. BRDU incorporation after blocking GFP+ cells with dnTCF. Non-transduced cells had significantly (p<0.001) greater BRDU incorporation than cells transduced with dnTCF.
Figure 9:
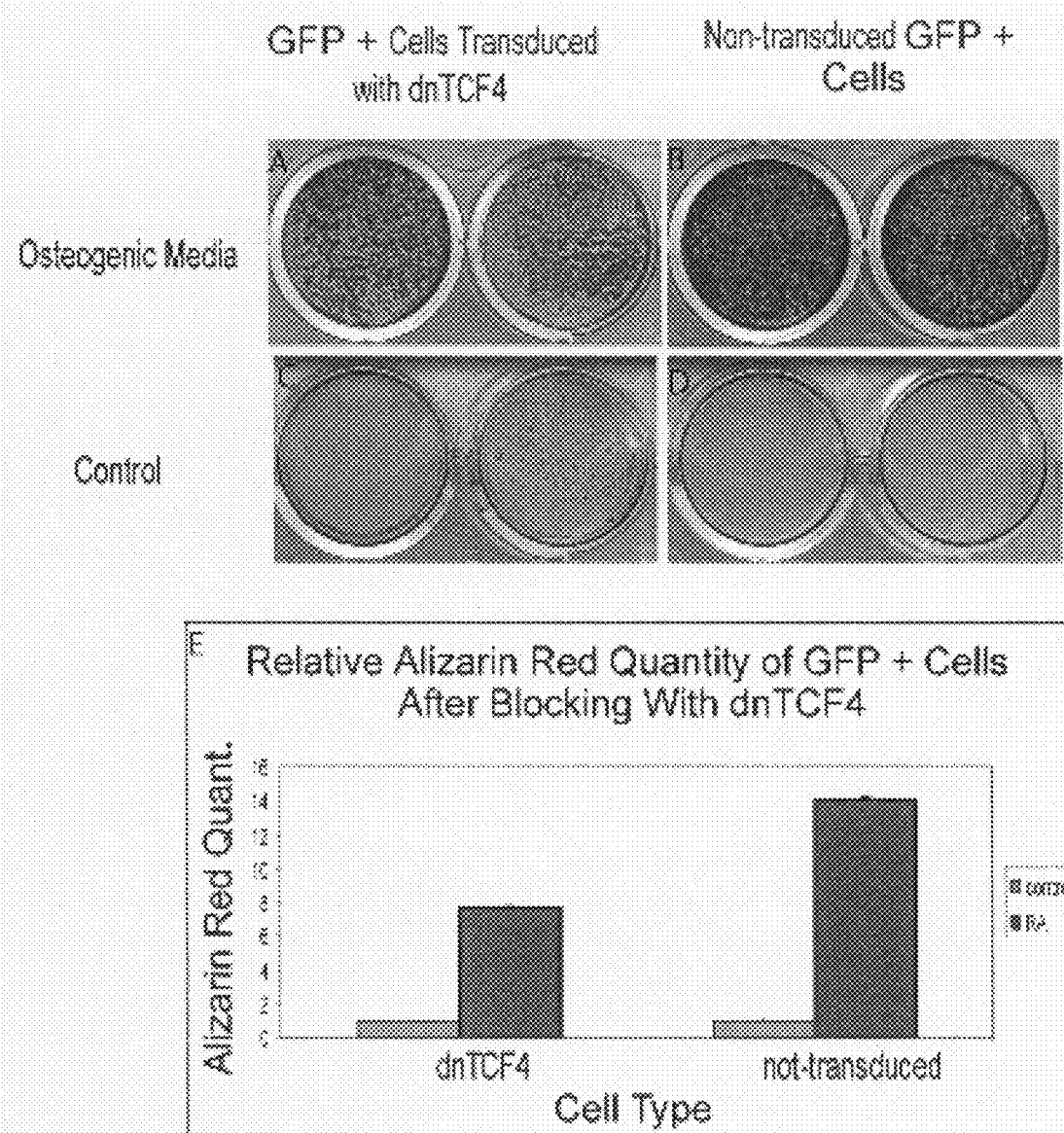
FIG. 9A-9E. Alizarin Red staining and quantification of β-catenin responsive cell with and without transduction with dnTCF. Cells transduced with dnTCF cultured in osteogenic media had deceased AR staining compared to non-transduced cells (A,B). Cells cultured in control media did not stain with AR (C,D). Alizarin Red quantification showed diminished AR in cells transduced with dnTCF as compared to non-transduced cells (p<0.05) (E).

Finally, in order to confirm the specific role of β-catenin in the observed phenotype of the GFP$^+$ cells, we performed the next set of experiments to block the β-catenin signal transduction pathway. The resorted GFP$^+$ cells, which were known to be capable of osteogenic and adipogenic differentiation, were transduced with a second lentiviral construct constitutively expressing a dominant negative TCF4 (dnTCF4). The β-catenin-binding domain of TCF4 is deleted, thus overexpression of this molecule will bind and block the target gene promoter sequences. We hypothesized that transduction of cells with this vector would therefore diminish the previously observed enhanced proliferation and differentiation phenotype. After transduction with the dnTCF lentivirus, resorted GFP$^+$ cells demonstrated decreased cell growth as indicated by decreased BRDU incorporation as compared to untransduced GFP+ resorted cells (FIG. 8). Transduction of these cells with the dnTCF4-expressing vector also resulted in decreased osteogenic differentiation, as indicated by alizarin red staining and quantification (FIG. 9). These findings indicate that the inhibition of β-catenin signaling in the enriched AMSC population abolished the previously observed progenitor phenotype.

Discussion

MSC biology has been extensively studied, but a certain degree of ambiguity remains given the numerous populations of heterogeneous cells examined to date. Taken together, the ability of a heterogeneous cohort of cells to undergo numerous cell doublings in culture, and to manifest multi-lineage differentiation capacity suggests that within a given MSC population there are stem cells or early progenitor cells that allow for the maintenance of the population's stem-like characteristics. In this study we have taken a novel approach utilizing a lentiviral reporter construct to separate and study subpopulations of MSC based on their functional response to the β-catenin signaling pathway.

In this study we have provided evidence that there exists within the MSC population a sub-population of β-catenin responsive cells that gives rise to both a β-catenin responsive (GFP+) and a β-catenin unresponsive (GFP−) population over serial in vitro passage. Upon purification of the GFP+ cells and subsequent culture, with increasing population doublings, the percentage of GFP+ cells diminishes, yet is eventually maintained at the same small percentage (2.1% of the total) as the starting mixed population of MSC. In the resorting experiments, we have confirmed that cells that were initially β-catenin un-responsive (GFP−), remain 100% GFP−. This establishes that the GFP− cells do not give rise to GFP+ cells and are therefore biologically incapable of returning to a state of β-catenin responsiveness. The early death of the β-catenin unresponsive cells after the resorting experiments results from the fact that these experiments eliminate the possibility that there might have been untransduced β-catenin responsive cells in the initial GFP− population. This further strengthens the evidence that β-catenin responsive cells are progenitors of GFP− cells, and are required for long term growth. The log-term proliferation characteristics of the GFP+ cells after the resorting experiments verify that as would be expected in a progenitor cell, the long-term proliferative capacity of these GFP+ cells is much greater than the GFP− subset of cells. The kinetics of change in percentage of β-catenin responsive cells and the maintenance of a small β-catenin responsive population at late passage, lends further support to the β-catenin responsive sub-population as containing the progenitor cells with self-renewal capacity. The more primitive nature of the GFP+ population is further supported by the observation that the GFP+ cells maintain bipotent differentiation capabilities for adipose and bone over a greater number of passages.

Given the variable Wnt signal transduction pathways both through β-catenin (canonical) and alternative pathways (non-canonical), we sought to determine if our enrichment strategy would reveal expected differences of the GFP+ cells response to exogenous Wnt proteins. The Wnt3a protein has previously been described to primarily signal through the β-catenin signal transduction pathway while regulating proliferative capacity and multi-potency. Conversely, the Wnt5a protein has been described as a differentiation factor, required for differentiation and maintenance of a mature cellular phenotype in several tissues, which signals through non-canonical pathways which increase calcium signaling.

In this study, the addition of exogenous canonical and non-canonical Wnt conditioned media had differential effects on the GFP+, cells as might be predicted by the described antagonistic role of these two proteins. As expected, exogenous Wnt5a protein conditioned media promoted osteogenic differentiation in both early passage GFP+ and GFP− subpopulations. Wnt3a conditioned media inhibited both osteogenic and adipogenic differentiation of the of GFP+ cells. This result substantiated our method of sub-population enrichment, confirming that enrichment of cells by responsiveness to β-catenin results in a demonstrable biologic effect in the GFP+ subset of cells. The observation that Wnt3a inhibited differentiation of the GFP+ MSC sub-population is consistent with its ascribed role as a factor that maintains potency by inhibiting differentiation as described for numerous other stem cell compartments, including in heterogeneous MSC, gut, skin, and blood.

In order to confirm our findings that an enriched population of MSC with expanded proliferative capacity and multi-lineage potency was conferred by the β-catenin/TCF/LEF gating mechanism described, we competitively inhibited target gene activation through a dominant negative approach to the TCF/LEF enhancer element utilized for β-catenin signal transduction. Competitive blocking of the β-catenin responsive cells with dnTCF4 led to inhibition of their growth and osteogenic differentiation. The decreased BRDU incorporation in the GFP+ progenitor subset as a result of blocking provides evidence that β-catenin mediated signaling is responsible for the progenitor like characteristic of increased proliferative capacity that are present in the β-catenin responsive cells. A block in β-catenin signal transduction did not enhance osteogenic differentiation as would be expected by diminished canonical Wnt signaling, rather it inhibited osteogenesis, as there was detectable less intense alizarin red staining in blocked cells. A possible explanation for this observation is that canonical signaling is not required for differentiation, thus allowing committed cells to continue differentiation. Additionally, if the dnTCF4 blocking of β-catenin promotes differentiation down the presumed default adipogenic pathway then this would result in diminished osteogenesis. In conclusion, dnTCF4 diminishes proliferative capacity of GFP+ progenitors and likely diminishes self-renewal thus resulting in decreased growth rates, and decreased osteogenesis.

This novel method of separating MSCs based on the activity of the β-catenin pathway provides a useful approach in identifying and isolating MSCs. The ability to enrich for multipotent progenitor cells allows in vitro studies of true "mesenchymal stem cells" or progenitors from this heterogeneous population so that a better understanding of their biological mechanisms can be obtained. Additionally, an understanding of the mechanisms that allow for self-renewal and govern maintenance of multipotency of MSCs will allow for advancement of their potential utility in tissue engineering and cell-based therapy.

Example 2

Figure 10:
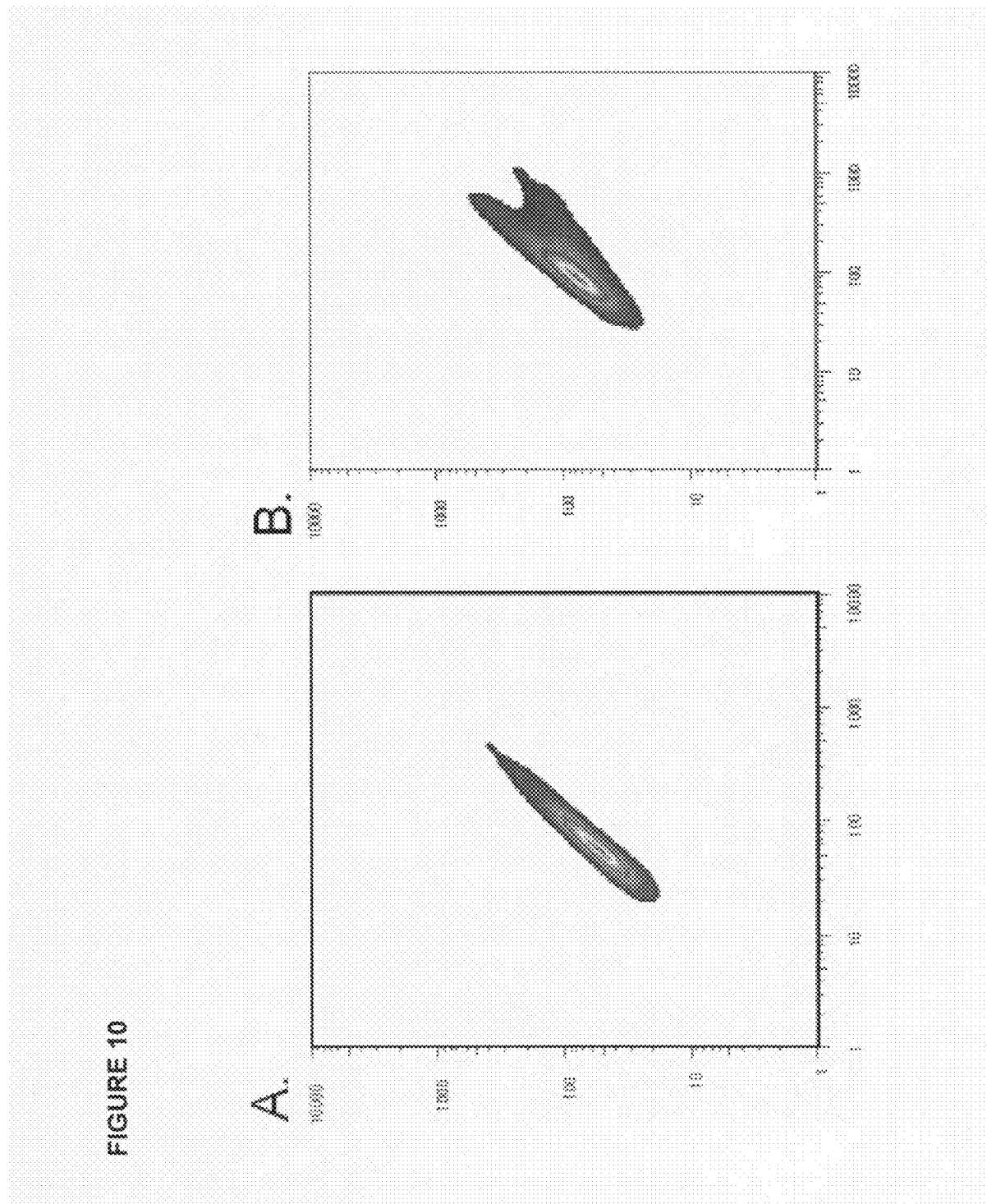
FIG. 10A-10B. FACS profile of human adipose derived multi-potent stromal cells in the absence or presence of a fluorescent β-catenin responsive reporter.

Freshly isolated human adipose derived multi-potent stromal cells (<P4) were plated and analyzed for GFP by FACS. As demonstrated in FIG. 10, there is a relatively homogeneous appearance of the cells without detectable GFP activity. After infection with the lentiviral reporter carrying six TCF/LEF1 binding sites driving GFP (SuperTOP), there is a minor population of cells that are recognized by the reporter as having active β-catenin/TCF/LEF activation in response to endogenous levels of ligands (FIG. 1).

Figure 11:
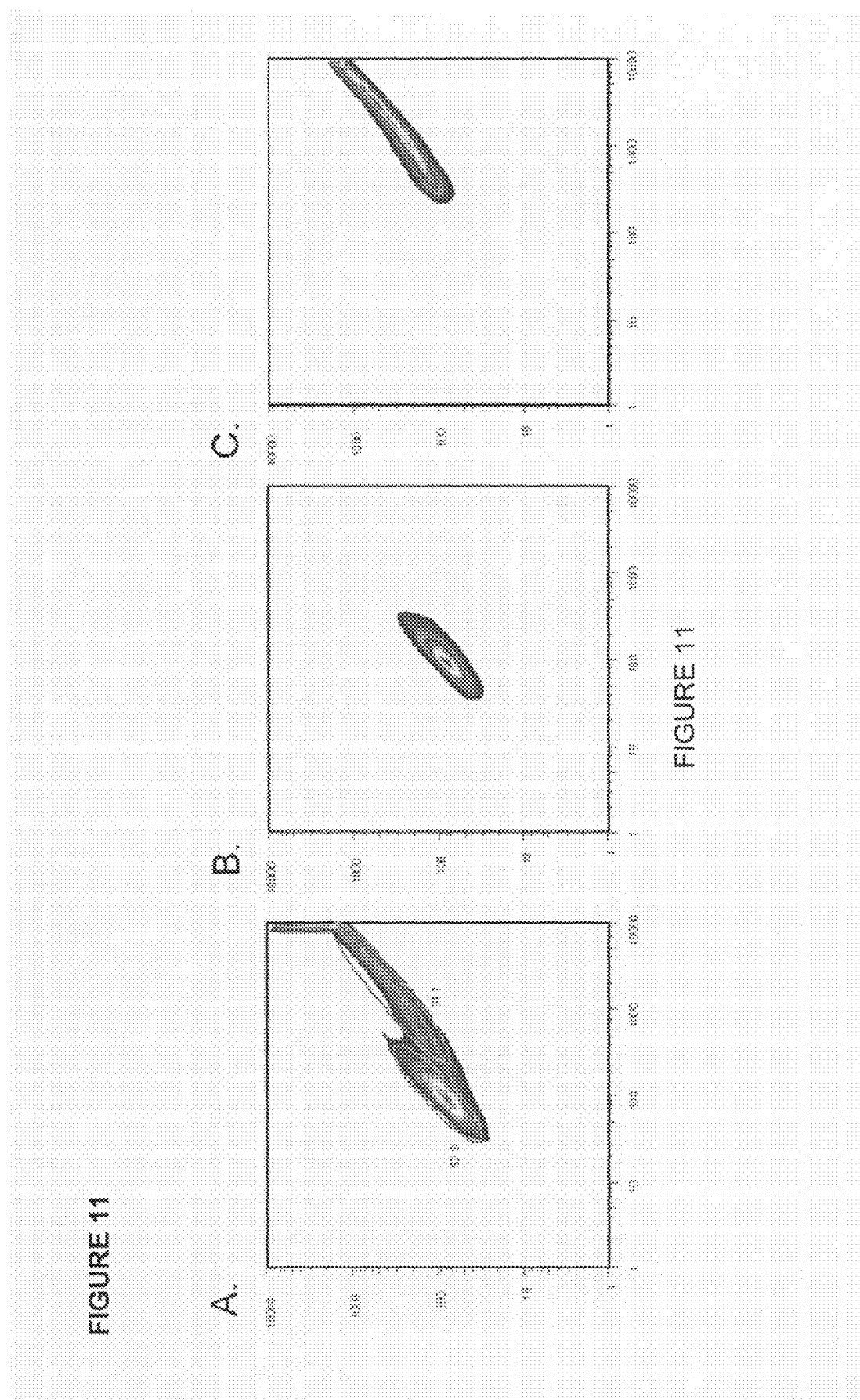
FIG. 11A-11C. FACS profile of human adipose derived multi-potent stromal cells stimulated with purified Wnt3a protein.

Next, these same cells were stimulated by purified Wnt3a protein (50 ng/ml). As shown in FIG. 11, the emergence of a highly responsive sub-population of cells to exogenous Wnt proteins can be identified by FACS (FIG. 11A). These sub-populations can be separated by FACS sorting and cultured separately (FIG. 11B,C)

What is claimed is:

1. A method for the isolation of mammalian mesenchymal stem cells (MSC) from bone marrow, the method comprising:
    introducing into an in vitro population of mammalian cells isolated from bone marrow a nucleic acid construct comprising sequences encoding a detectable marker, which marker is operably linked to a transcriptional response element regulated by β-catenin, wherein said transcriptional response element is a LEF-1/TCF binding sequence;
    detecting the presence of expression of said detectable marker;
    selecting for cells expressing said detectable marker; and
    wherein expression of said marker is indicative that a cell is an MSC.

2. The method according to claim 1, wherein said marker is a fluorescence producing protein.

3. The method according to claim 1, further comprising the step of culturing cells expressing said detectable marker in vitro.

4. The method according to claim 3,, wherein said in vitro culture provides non-differentiating conditions.

5. The method according to claim 3, wherein said in vitro culture provides differentiating conditions.

6. The method according to claim 5, wherein said culture conditions induce differentiation of at least one of chondrocytes, adipocytes, osteocytes and myocytes.

7. The method according to claim 4, further comprising the steps of:
    culturing said cells for at least one passage; and
    selecting for cells expressing said detectable marker.

8. The method according to claim 7, wherein the selected cells remain non-differentiated for at least five passages in culture.

* * * * *